United States Patent
Jeary et al.

(10) Patent No.: US 7,465,462 B1
(45) Date of Patent: Dec. 16, 2008

(54) MULTIPARTICULATE CONTROLLED RELEASE SELECTIVE SEROTONIN REUPTAKE INHIBITOR FORMULATIONS

(75) Inventors: Theresa Ann Jeary, Roscommon (IE); Catherine Ann Morrissey, County Westmeath (IE); Paul Stark, County Westmeath (IE)

(73) Assignee: Elan Pharma International Limited, Monksland Athlone County Westmeath (IL)

( * ) Notice: Subject to any disclaimer, the term of this patent is extended or adjusted under 35 U.S.C. 154(b) by 0 days.

(21) Appl. No.: 09/744,169

(22) PCT Filed: May 10, 2000

(86) PCT No.: PCT/IE00/00060

§ 371 (c)(1), (2), (4) Date: Apr. 19, 2001

(87) PCT Pub. No.: WO00/71099

PCT Pub. Date: Nov. 30, 2000

(30) Foreign Application Priority Data

May 20, 1999 (IE) .................................. 990406

(51) Int. Cl.
*A61K 9/14* (2006.01)
(52) U.S. Cl. .................. 424/489; 424/451; 424/457; 424/459; 424/464; 424/468; 424/490; 424/493; 424/494; 424/495
(58) Field of Classification Search .................. 424/464, 424/489, 490, 497
See application file for complete search history.

(56) References Cited

U.S. PATENT DOCUMENTS

| | | | | |
|---|---|---|---|---|
| 4,085,225 A | | 4/1978 | Welle et al. .................. 424/304 |
| 4,851,228 A | * | 7/1989 | Zentner et al. ............... 424/456 |
| 5,133,974 A | | 7/1992 | Paradissis et al. | |
| 5,271,946 A | * | 12/1993 | Hettche ....................... 424/490 |
| 5,445,829 A | | 8/1995 | Paradissis et al. | |
| 5,776,969 A | * | 7/1998 | James .......................... 514/418 |
| 5,948,440 A | * | 9/1999 | Arora et al. ................... 524/468 |
| 5,958,458 A | * | 9/1999 | Norling et al. ............... 424/490 |
| 6,066,339 A | * | 5/2000 | Stark et al. ................... 424/489 |
| 6,080,736 A | * | 6/2000 | Landry et al. ................ 514/221 |
| 6,183,780 B1 | * | 2/2001 | Van Balken et al. ......... 424/480 |
| 6,306,436 B1 | * | 10/2001 | Chungi et al. ............... 424/464 |
| 6,458,384 B2 | * | 10/2002 | Jaenicke et al. .............. 424/468 |
| 6,482,440 B2 | * | 11/2002 | Zemlan et al. ............... 424/489 |

FOREIGN PATENT DOCUMENTS

| | | | |
|---|---|---|---|
| EP | 0 797 991 | * | 10/1997 |
| EP | 0 797 991 A | | 10/1997 |
| GB | 2 325 623 | * | 12/1998 |
| GB | 2 325 623 A | | 12/1998 |
| WO | 97 03670 A | | 2/1997 |
| WO | 99 01121 A | | 1/1999 |
| WO | 99 01122 A | | 1/1999 |
| WO | WO 9901122 A1 | * | 1/1999 |
| WO | WO 9912524 A1 | * | 3/1999 |

OTHER PUBLICATIONS

Davidson, Jonathan et al, "Fluvoxamine-Controlled Release Formulation for the Treatment of Generalized Social Anxiety Disorder," J. Clin. Psychopharmacol, vol. 24(2), pp. 118-125, Apr. 2004.
Westenberg, Herman et al , "A Double-Blind Placebo-Controlled Study of Controlled Release Fluvoxamine for the Treatment of Generalized Social Anxiety Disorder," Journal of Clinical Psychopharmacology, vol. 24(1), pp. 49-55, Feb. 2004.
Hollander, Eric et al , "A Double-Blind Placebo-Controlled Study of the Efficacy and Safety of Controlled-Release Fluvoxamine in Patients With Obsessive-Compulsive Disorder," J. Clin. Psychiatry, 64:6, pp. 640-647, Jun. 2003.

* cited by examiner

*Primary Examiner*—S. Tran
(74) *Attorney, Agent, or Firm*—Fox Rothschild LLP

(57) ABSTRACT

A multiparticulate controlled release selective serotonin reuptate inhibitor (SSRI) formulation for oral administration is provided. The formulation includes particles of an SSRI or a pharmaceutically acceptable salt thereof, which are coated with a rate-controlling polymer that allows controlled release of the SSRI over a period of not less than about 12 hours after oral administration. The rate controlling polymer includes a film-forming water-insoluble polymer, or a mixture of a film-forming water-insoluble polymer and a film-forming water-soluble polymer.

45 Claims, 5 Drawing Sheets

MULTIPARTICULATE CONTROLLED RELEASE SELECTIVE SEROTONIN REUPTAKE INHIBITOR FORMULATIONS

This application claims the benefit under 35 U.S.C. § 119(a) of the filing date for Republic of Ireland application number 990406, filed on May 20, 1999, and the benefit under 35 U.S.C. § 365(a) of the filing date for PCT international application number PCT/IE00/00060, filed on May 10, 2000.

TECHNICAL FIELD

This invention relates to controlled release pharmaceutical formulations and, in particular, to controlled release forms of fluvoxamine and other selective serotonin reuptake inhibitors, for oral administration.

BACKGROUND ART

Selective serotonin reuptake inhibitors, SSRIs (typified by fluoxetine, fluvoxamine, paroxetine and sertraline) are used inter alia as antidepressants. In the following description reference will be made collectively to fluvoxamine when referring to SSRIs, except where otherwise stated.

Fluvoxamine maleate is a selective serotonin (5HT) reuptake inhibitor belonging to the 2-aminoethyl oxime ethers of aralkylketones chemical series. It is chemically designated as 5-methoxy-4'-(trifluoromethyl)valerophenone-(E)-O-(2-aminoethyl)oxime maleate (1:1) and has the empirical formula $C_{15}H_{21}O_2N_2F_3.C_4H_4O_4$. Fluvoxamine and other oxime ethers are disclosed in U.S. Pat. No. 4,085,225 (US Philips Corp.). Tablet, suppository and injection formulations are described.

Fluvoxamine has been shown to be effective in alleviating the symptoms of depression and in the treatment of obsessive compulsive disorder. It is conventionally administered in tablet form (25 mg, 50 mg and 100 mg) as fluvoxamine maleate sold under the Trade Mark Luvox (Solvay Pharmaceuticals Inc.). Conventional fluvoxamine therapy typically starts with 50 mg administered as a single dose at bedtime. The dosage may be gradually increased in 50 mg increments every 4 to 7 days, as tolerated, until maximum therapeutic benefit is achieved, not to exceed 300 mg per day. It is advisable that a total daily dose of more than 100 mg should be given in two divided doses. If the doses are not equal, the larger dose is typically given at bedtime.

Fluvoxamine is extensively metabolised by the liver and excreted by the kidneys in urine. Luvox® is subject to extensive first pass effect, typically giving an absolute bioavailability of about 53%. Typically single oral doses of Luvox® result in peak plasma levels 3 to 8 hours after administration. The plasma elimination half-life of fluvoxamine at steady state after multiple oral doses of 100 mg/day in healthy, young volunteers is reported to be 15.6 hours.

As stated above, conventional fluvoxamine tablets are currently titrated gradually to a tolerated dose with maximum therapeutic benefit, with doses of greater than 100 mg given in two divided doses. The gradual titration and adverse events related to conventional once-daily dosing of doses greater than 100 mg may reduce patent compliance and delay the onset of therapeutic benefit.

It is an object of the present invention therefore to provide a controlled release selective serotonin (5HT) reuptake inhibitor formulation.

It is another object of the present invention to provide a controlled release SSRI formulation suitable for administration no more frequently than on the average than at twelve hour intervals.

It is another object of the present invention to provide a controlled release SSRI formulation suitable for once or twice daily administration.

A further object of the present invention is to provide a method of treatment of depression and/or obsessive compulsive disorder.

DISCLOSURE OF INVENTION

The invention provides a multiparticulate controlled release selective serotonin reuptake inhibitor (SSRI) formulation for oral administration, which comprises particles of said SSRI or a pharmaceutically acceptable salt thereof coated with rate-controlling polymer which allows controlled release of said SSRI over a period of not less than about 12 hours following oral administration.

Preferably, the particles are pellets or beads.

Further, preferably, said pellets comprise a core of said SSRI or a pharmaceutically acceptable salt thereof coated with said rate-controlling polymer to form a rate-controlling membrane surrounding said core.

According to one embodiment the rate-controlling membrane is made up of a major proportion of a pharmaceutically acceptable film-forming, water-insoluble polymer and optionally a minor proportion of a pharmaceutically acceptable film-forming, water-soluble polymer, the ratio of said water-insoluble polymer to said water-soluble polymer, when said water-soluble polymer is present, being effective to permit a SSRI release rate which allows controlled release of SSRI over a period of not less than about 12 hours following oral administration.

The membrane can, however, consist of a pharmaceutically acceptable film-forming, water-insoluble polymer. Alternatively, the membrane can comprise a mixture of rate-controlling polymers consisting of a major proportion of a pharmaceutically acceptable film-forming, water-insoluble polymer and a minor proportion of a pharmaceutically acceptable film-forming, water soluble polymer.

The polymers that can be used to form the rate-controlling membrane are described in greater detail hereinbelow.

According to an especially preferred embodiment the rate-controlling membrane contains an ammonio methacrylate co-polymer as hereinafter described.

The core can comprise an organic acid, the SSRI component and the organic acid being present in a ratio of from 50:1 to 1:50.

The organic acid, when such is used, is preferably selected from adipic acid, ascorbic acid, citric acid, fumaric acid, malic acid, succinic acid and tartaric acid. The SSRI component and the organic acid, when present, are preferably present in a ratio of from 20:1 to 1:1 and more preferably in a ratio of from 10:1 to 2:1.

The active ingredient in the formulation according to the present invention can suitably comprise any selective serotonin reuptake inhibitor. Particularly suitable active ingredients for use in the present invention include those selected from: citalopram, clomipramine, fluoxetine, fluvoxamine, paroxetine, sertraline, trazodone, venlafaxine and zimeldine, all of which inhibit serotonin reuptake to various degrees.

The active ingredient can be present in the form of a free base or in the form of a pharmaceutically acceptable salt such as the hydrochloride or a maleate form.

Further, the active ingredient, where applicable, may be present either in the form of one substantially optically pure enantiomer or as a mixture, racemic or otherwise, of enantiomers.

A preferred SSRI is fluvoxamine or a pharmaceutically acceptable salt thereof.

According to one embodiment the SSRI release rate from the particles when measured in vitro using a USP type II dissolution apparatus (paddle) according to US Pharmacopoeia XXII in 0.05 M phosphate buffer at pH 6.8 substantially corresponds to the following dissolution pattern:

(a) No more than 15% of the total SSRI is released after 0.5 of an hour of measurement in said apparatus;
(b) No more than the 25% of the total of SSRI is released after 1 hour of measurement in said apparatus;
(c) Between 20% and 75% of the total SSRI is released after 2 hours of measurement in said apparatus;
(d) Not less than 75% of the total SSRI is released after 4 hours of measurement in said apparatus; and
(e) Not less than 85% of the total SSRI is released after 6 hours of measurement in said apparatus.

According to another embodiment the SSRI release rate from the particles when measured in vitro using a USP type II dissolution apparatus (paddle) according to US Pharmacopoeia XXII in 0.05 M phosphate buffer at pH 6.8 substantially corresponds to the following dissolution pattern:

(a) No more than 20% of the total SSRI is released after 4 hours of measurement in said apparatus;
(b) No more than 45% of the total SSRI is released after 6 hours of measurement in said apparatus;
(c) Between 45% and 80% of the total SSRI is released after 8 hours of measurement in said apparatus;
(d) Not less than 70% of the total SSRI is released after 10 hours of measurement in said apparatus; and
(e) Not less than 80% of the total SSRI is released after 12 hours of measurement in said apparatus.

The core optionally contains a lubricant such as, for example, sodium stearate, magnesium stearate, stearic acid or talc.

Preferably, the core comprises the SSRI or a pharmaceutically acceptable salt thereof and the associated organic acid, when present, embedded in a polymeric material or binder, hereinafter referred to as the polymeric material, except where otherwise stated. The SSRI component and the polymeric material are preferably present in a ratio of from 1:1 to 100:1, more particularly from 5:1 to 30:1. The polymeric material may be rapidly soluble in water or, alternatively, may be freely permeable to SSRI and water. However, the polymeric material may also be insoluble in water or, alternatively, may be slightly permeable to SSRI and water. Mixtures of any of the aforementioned polymers may also be used provided that the polymer(s) used is/are effective to ensure that all of the SSRI is coated onto the core. The ratio of water soluble/freely permeable to water insoluble/slightly permeable polymer may be determined by the particular combination of polymers selected.

Suitably, the core comprises:

(a) a powder mixture containing the SSRI or a pharmaceutically acceptable salt thereof, an organic acid selected from adipic acid, ascorbic acid, acid, fumaric acid, malic acid, succinic acid and tartaric acid; and
(b) a pharmaceutically acceptable polymeric material, said polymeric material being present in an amount effective to ensure that all of the powder mixture is coated onto the core.

The core can comprise layers of said powder mixture and said polymeric material superimposed one upon the other.

The term water soluble polymer as used herein includes polymers which are freely permeable to water such as Eudragit RL. Likewise, the term water insoluble polymer as used herein includes polymers which are slightly permeable to water such as Eudragit RS.

The water soluble polymer is suitably polyvinyl alcohol, polyvinylpyrrolidone, methylcellulose, hydroxypropylcellulose, hydroxypropylmethyl cellulose or polyethylene glycol, or a mixture thereof.

The water insoluble polymer is suitably ethylcellulose, cellulose acetate cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), and poly(hexyl methacrylate). poly(isodecyl methacrylate), poly(lauryl methacrylate), poly(phenyl methacrylate), poly (methyl acrylate), poly(isopropyl acrylate), poly(isobutyl acrylate), poly(octadecyl acrylate), poly(ethylene). poly(ethylene) low density, poly(ethylene) high density, poly(ethylene oxide), poly(ethylene terphthalate). poly(vinyl isobutyl ether), poly(vinyl acetate), poly(vinyl chloride) or polyurethane, or a mixture thereof.

A suitable polymer which is freely permeable to fluvoxamine and water is a polymer sold under the Trade Mark Eudragit® RL. A suitable polymer which is slightly permeable to fluvoxamine and water is a polymer sold under the Trade Mark Eudragit® RS or a polymer whose permeability is pH dependent such as those sold under the Trade Marks Eudragit® L, Eudragit® S or Eudragit® E. Eudragit® polymers are polymeric lacquer substances based on acrylate and/or methacrylates.

Polymeric materials sold under the Trade Marks Eudragit® RL and Eudragit® RS are acrylic resins comprising copolymers of acrylic and methacrylic acid esters with a low content of quaternary ammonium groups (as described in the "Eudragit®" brochure of Rohm Pharma GmbH (1985)). The ammonium groups are present as salts and give rise to the permeability of the lacquer films. Eudragit® RL and RS are freely permeable (RL) and slightly permeable (RS), respectively, independent of pH. Eudragit® L is an anionic polymer synthesized from methacrylic acid and methacrylic acid methyl ester. It is insoluble in acids and pure water. It becomes soluble in neutral to weakly alkaline conditions. The permeability of Eudragit® L is pH dependent. Above pH 5.0, the polymer becomes increasingly permeable. (Eudragit® L is described in the "Eudragit® L" brochure of Rohm Pharma GmbH (1986)).

The polymers Eudragit S and Eudragit L can be combined in the one coating film in any ratio. By using a combination of the polymers theoretically results in coating films which are soluble at a pH between the pHs at which Eudragit L and Eudragit S are soluble.

The polymeric material of the core can consist solely of Eudragit RS as hereinafter exemplified.

The SSRI, organic acid, when such is present, and polymeric material are preferably built up on a central inert core. The core suitably consists of a non-pareil bead of sugar/starch having an average diameter in the range of from 0.4 to 0.85 mm, typically from 0.71 to 0.85 mm for a formulation where the organic acid is not present and typically from 0.6 to 0.71 mm for a formulation where the organic acid is present. The actual bead size used may vary depending on the drug/organic acid loading required for a particular formulation. The core may be built up in a conventional coating pan. Alternatively, the SSRI, organic acid and polymeric material may be built up on a central inert core as hereinbefore defined in an automated coating system for example, a CF granulator. The core may also include further components to those specified above such as a dispersing agent, glidant and/or surfactant.

The polymeric coating used to form the rate-controlling membrane can also include one or more auxiliary agents selected from a filler, a plasticiser and an anti-foaming agent.

Representative fillers include talc, fumed silica, glyceryl monostearate, magnesium stearate, calcium stearate, kaolin, colloidal silica, gypsum, micronised silica and magnesium trisilicate.

Talc is the preferred filler.

The quantity of filler used is from about 2% to about 500% by weight, preferably from 100 to 450%, more particularly 410 to 440%, based on the total dry weight of the polymer.

The polymeric coating can also include a material that improves the processing of the polymers. Such materials are generally referred to as "plasticisers" and include, for example, adipates, azelates, benzoates, citrates, isoebucates, phthalates, sebacates, stearates and glycols.

Representative plasticisers include acetylated monoglycerides; butyl phthalyl butyl glycolate; dibutyl tartrate; diethyl phthalate; dimethyl phthalate; ethyl phthalyl ethyl glycolate; glycerin; ethylene glycol, propylene glycol; triacetin citrate; triacetin; tripropinoin; diacetin; dibutyl phthalate; acetyl monoglyceride; polyethylene glycols; castor oil; triethyl citrate; polyhydric alcohols, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, glyceryl monocaprylate and glyceryl monocaprate.

Dibutyl sebacate is the preferred plasticiser.

The amount of plasticiser to be used is preferably from about 10% to 50%, most preferably about 20%, based on the weight of the dry polymer.

An example of an anti-foaming agent is Simethicone. The amount of anti-foaming agent to be used in the coating is preferably from 0% to 0.5% of the final formulation.

The amount of polymer to be used in forming the particles will be determined by the desired delivery properties, including the amount of drug to be delivered, the release rate desired, and the size of the particles. The membrane polymers will be coated to 10 to 100% weight gain on the cores, preferably 25-70% polymer weight gain. The rate-controlling membrane on the particles, including all solid components thereof such as co-polymer, filler, plasticiser and optional additives and processing aids, is from about 11% to 450% weight gain on the cores, preferably 30% to 160% weight gain. The polymer layer can be coated by any known method, including spray application. Spraying can be carried out using a fluidised bed coater (preferably Wurster coating), or in a pan coating system.

The coated cores are dried or cured after application of the polymer layer(s). "Curing" means that the particles are held at a controlled temperature for a time sufficient to provide stable release rates. Curing can be performed for example in an oven or in a fluid bed drier. Curing can be carried out at any temperature above room temperature.

A sealant or barrier layer can be applied to the polymeric coating.

The sealant or barrier layer may be applied to the polymeric coating to prevent agglomeration of the particles.

The core is suitably coated with a polymeric rate-controlling membrane comprising at least one polymeric material as described above. The core may be coated to any coating level which is sufficient to facilitate the desired release rate.

The rate-controlling membrane can comprise a single polymer or a mixture of two or more polymers.

The water insoluble polymer of the membrane is any one of those hereinbefore specified for the core and includes polymers which are slightly permeable or impermeable to water as hereinbefore described.

Likewise the water soluble polymer of the membrane is any one of those hereinbefore specified for the core and includes polymers which are freely permeable to water as hereinbefore described.

Ammonio methacrylate co-polymers which include polymers sold under the Trade Marks Eudragit RS and Eudragit RL by Rohm & Haas referred to above are particularly suitable for use in the rate-controlling membrane in the formulations according to the invention. These polymers are insoluble in pure water, dilute acids, buffer solutions or digestive fluids over the entire physiological pH range. The films swell in water (and digestive fluids independently of pH). In the swollen state they are then permeable to water and dissolved actives. The permeability of the films depends on the ratio of ethylacrylate (EA), methyl methacrylate (MMA) and trimethylammonioethyl methacrylate chloride (TAMCl) groups in the polymer. Those polymers having EA:MMA:TAMCl ratios of 1:2:0.2 (Eudragit RL) are more permeable than those with ratios of 1:2:0.1 (Eudragit RS). Films of Eudragit RL are described as being "insoluble films of high permeability" and films of Eudragit RS are described as being "insoluble films of low permeability".

Oral dosage forms of the controlled release SSRI formulation of the invention can be in the form of a multiparticulate formulation or a tablet. The term "multiparticulate" as used herein includes discrete particles, pellets, mini-tablets and mixtures or combinations thereof. A multiparticulate oral dosage form according to the invention can comprise a blend of two or more populations of particles, pellets or mini-tablets having different in vitro and/or in vivo release characteristics. For example, the multiparticulate oral dosage form can comprise a blend of an instant release component and a controlled release component contained in a suitable capsule, for example hard or soft gelatin capsules. If the multiparticulate formulation is filled into a capsule it may be administered by swallowing the capsule or by opening said capsule and sprinkling the contents onto food. Alternatively the multiparticulate may be presented in a sachet.

The particles and one or more auxiliary excipient materials can be compressed into tablet form such as a multilayer tablet. Typically a multilayer tablet may comprise two layers which may contain the same or different levels of the same active ingredient having the same or different release characteristics or may contain a different active ingredient in each layer. Such a multilayer tablet may optionally be coated with a controlled release polymer so as to provide additional controlled release properties.

As indicated above the controlled release SSRI formulations and oral dosage forms of the present invention may comprise auxiliary excipients such as for example diluents, lubricants, surfactants, disintegrants, plasticisers, anti-tack agents, opacifying agents, pigments, flavourings and such like. As will be appreciated by those skilled in the art, the exact choice of excipients and their relative amounts will depend to some extent on the final oral dosage form into which the controlled release SSRI formulation is incorporated.

Suitable diluents include for example pharmaceutically acceptable inert fillers such as microcrystalline cellulose, lactose, dibasic calcium phosphate, saccharides, and/or mixtures of any of the foregoing. Examples of diluents include microcrystalline celluloses such as those sold under the Trade Mark Avicel; including for example Avicel pH101, Avicel pH102, Avicel pH112, Avicel pH200, Avicel pH301 and Avicel pH302; lactose such as lactose monohydrate, lactose anhydrous and Pharmatose DCL21 (Pharmatose is a Trade Mark), including anhydrous, monohydrate and spray dried forms; dibasic calcium phosphate such as Emcompress (Emcompress is a Trade Mark); mannitol; starch; sorbitol; sucrose; and glucose.

Suitable lubricants, including agents that act on the flowability of the powder to be compressed are, for example, colloidal silicon dioxide such as Aerosil 200 (Aerosil is a Trade Mark); talc; stearic acid, magnesium stearate, calcium stearate and sodium stearyl fumarate.

Suitable disintegrants include for example lightly crosslinked polyvinyl pyrrolidone, corn starch, potato starch, maize starch and modified starches, croscarmellose sodium, cross-povidone, sodium starch glycolate and combinations and mixtures thereof.

According to a further aspect of the invention there is provided a controlled release SSRI formulation for oral administration comprising a blend of particles as hereinbefore defined.

According to a still further aspect of the invention there is provided a controlled release SSRI formulation for oral administration comprising a blend of particles as hereinbefore defined in admixture with an immediate release form of SSRI or a pharmaceutically acceptable salt thereof to ensure a rapid attainment of effective therapeutic blood levels.

Preferably, the immediate release form of SSRI comprises pellets as hereinbefore defined without said rate-controlling membrane.

According to one embodiment the SSRI release rate from the formulation when measured in vitro using a USP type II dissolution apparatus (paddle) according to US Pharmacopoeia XXII in 0.05 M phosphate buffer at pH 6.8 substantially corresponds to the following dissolution pattern:

(a) No more than 20% of the total SSRI is released after 1 hour of measurement in said apparatus;
(b) No more than 60% of the total SSRI is released after 2 hours of measurement in said apparatus;
(c) Not less than 20% of the total SSRI is released after 4 hours of measurement in said apparatus;
(d) Not less than 35% of the total SSRI is released after 6 hours of measurement in said apparatus;
(e) Not less than 50% of the total SSRI is released after 8 hours of measurement in said apparatus;
(f) Not less than 70% of the total SSRI is released after 10 hours of measurement in said apparatus; and
(g) Not less than 75% of the total SSRI is released after 12 hours of measurement in said apparatus.

According to another embodiment the SSRI release rate from the formulation when measured in vitro using a USP type II dissolution apparatus (paddle) according to US Pharmacopoeia XXII in 0.05 M phosphate buffer at pH 6.8 substantially corresponds to the following dissolution pattern:

(a) No more than 20% of the total SSRI is released after 1 hour of measurement in said apparatus;
(b) No more than 45% of the total SSRI is released after 2 hours of measurement in said apparatus;
(c) Between 20% and 70% of the total SSRI is released after 4 hours of measurement in said apparatus;
(d) Between 35% and 85% of the total SSRI is released after 6 hours of measurement in said apparatus;
(e) Not less than 50% of the total SSRI is released after 8 hours of measurement in said apparatus;
(f) Not less than 70% of the total SSRI is released after 10 hours of measurement in said apparatus; and
(g) Not less than 75% of the total SSRI is released after 12 hours of measurement in said apparatus.

According to a still further embodiment the SSRI release rate from the formulation when measured in vitro using a USP type II dissolution apparatus (paddle) according to US Pharmacopoeia XXII in 0.05 M phosphate buffer at pH 6.8 substantially corresponds to the following dissolution pattern:

(a) No more than 50% of the total SSRI is released after 2 hours of measurement in said apparatus;
(b) Not less than 35% of the total SSRI is released after 6 hours of measurement in said apparatus; and
(c) Not less than 80% of the total SSRI is released after 22 hours of measurement in said apparatus.

A formulation for once-daily administration may comprise a blend of a controlled release formulation as hereinbefore defined together with up to 75% by weight of an immediate release form of said SSRI, preferably from about 10% to 50% by weight.

According to a still further aspect of the invention there is provided a method for the treatment of depression, obsessive compulsive disorder or other condition treatable with an SSRI, comprising administering to a patient suffering from one of said conditions a therapeutically effective amount of a multiparticulate controlled release SSRI formulation.

To avoid repetition the invention will be described in further detail with reference to fluvoxamine as a specific example.

Figure 1:
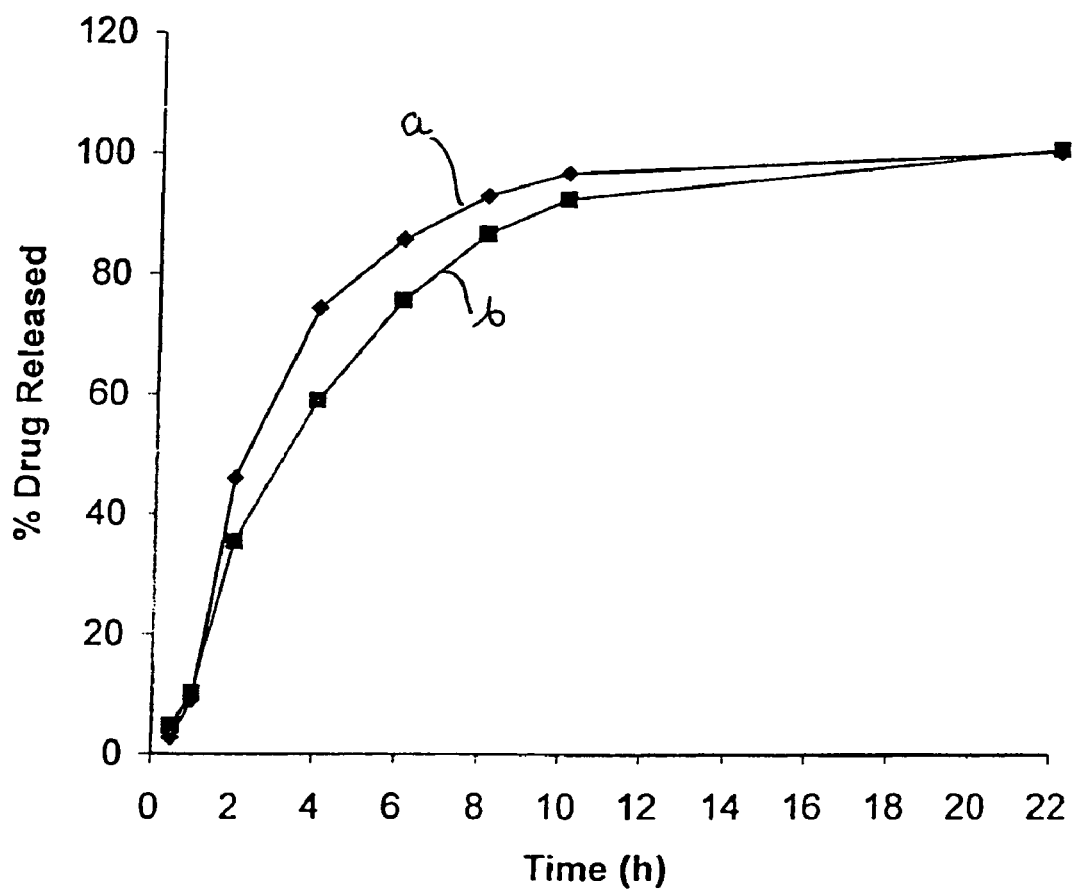
FIG. 1 is a plot of % drug released versus time (h) for the controlled release capsules of Example 2.

The invention will be further illustrated by the following Examples.

MODES FOR CARRYING OUT THE INVENTION

Example 1

Production of Four Fluvoxamine Controlled Release Multiparticulate Formulations

Manufacture of Drug Loaded Beads.

Two drug loaded bead batches were manufactured, 1 and 2 respectively, and the formulation details are set out in Table 1.

Batch 2 was selected for the manufacture of controlled release (CR) beads. This batch was chosen over Batch 1 because it showed a faster release of drug hence it was deemed more suitable as an immediate release (IR) portion.

TABLE 1

Formulation Details for Fluvoxamine Drug Loaded Beads.

| | Batch No. | |
|---|---|---|
| Composition | 1 (Kg) | 2 (Kg) |
| Fluvoxamine Maleate | 12.450 | 12.450 |
| Talc | 3.550 | 3.550 |
| (% of active) | 28.5% | 28.5% |
| Total | 16.000 | 16.000 |
| Non-Pareil Seeds (0.71-0.85 mm) | 5.000 | 5.000 |
| Eudragit RS (12.5% Polymer Solids) | 1.618 | 1.413 |

The drug loaded beads were manufactured by blending the fluvoxamine maleate and talc for 5 min. to a homogeneous powder in an E 5904 Blender. The homogenous powder and the Eudragit RS sprayed sugar seeds were applied simultaneously to non-pareil seeds. The beads were oven dried at 55° C. for 20 h. to remove solvent. The beads were then sieved to remove agglomerates.

The drug loaded beads so produced were evaluated for potency and dissolution. Dissolution testing was conducted on USP Apparatus 2, using 900 ml of pH 6.8 phosphate buffer and a paddle speed of 50 rpm. All testing was replicated by six.

Table 2 details the potency results. Based on the potency results, a drug loading of 53% was achieved using 0.71-0.85 mm non-pareil seeds.

TABLE 2

Potency Results for Fluvoxamine 100 mg Drug Loaded Beads

| Batch No. | Actual Potency (mg/g) |
|---|---|
| 1 | 537.6 |
| 2 | 530.1 |

The dissolution results are summarised in Table 3. The results satisfy the USP specifications for immediate release products of ≧75% released in 45 min. (e.g. Batch 1 97.2% released after 45 min.; Batch 2: 99.1% released after 45 min.). Due to the fact that Batch 2 illustrated a better dissolution profile this batch was selected for coating to produce controlled release beads.

TABLE 3

Dissolution Results for Fluvoxamine 100 mg Drug Loaded Beads

| | Batch No. | |
|---|---|---|
| Time (min.) | 1 | 2 |
| | % Released | |
| 15 | 87.0 | 88.7 |
| 30 | 93.9 | 96.1 |
| 45 | 97.2 | 99.1 |
| 60 | 97.1 | 99.7 |
| 120 | 99.2 | 101.6 |

Manufacture of Controlled Release Beads.

Controlled release beads were produced by the polymeric coating of the drug loaded beads. The polymer coating solution and talc were applied simultaneously at controlled rates. The application of talc at this stage prevents agglomeration of the beads during the coating process.

During the process, beads were sampled at 4%, 6%, 8%, 10%, 12% and 15% levels of polymer coat.

The formulation details for the batch produced are set out in Table 4. The coating polymer formulation details for fluvoxamine 100 mg CR beads are summarised in Table 5. The stages involved in the manufacture of controlled release beads are as follows, the drug loaded beads were coated in a CF750 Coater with the polymer coating solution made up of Eudragit RS with isopropyl alcohol (IPA) and dibutyl sebacate (DBS) as plasticiser in the presence of talc to prevent agglomeration. The beads were oven dried at 55° C. for 20 h. to remove solvent residues. The beads were then sieved to remove agglomerates, from the controlled release beads.

TABLE 4

Formulation Details For Fluvoxamine 100 mg CR Beads

| Composition | Kg |
|---|---|
| Fluvoxamine IR Beads | 15.000 |
| Talc | 9.0669 |
| (% of polymer solids) | (504.5) |
| Eudragit RS + DBS | 29.1625 |
| Coating solution | |
| (6.17% polymer solids) | (1.797) |

TABLE 5

Formulation Details of Polymer Used in the Manufacture of Fluvoxamine 100 mg CR Beads.

| Coating Solution Composition | Eudragit RS + Plasticiser (Kg) |
|---|---|
| Eudragit RS(12.5) | 18.000 |
| I.P.A. | 18.000 |
| DBS | 0.450 |
| TOTAL | 36.450 |

Potency and Dissolution testing were performed on the manufactured CR beads (i.e. 4%, 6%, 8%, 10%, 12% and 15%). Dissolution testing was performed using USP Apparatus 2, with 900 ml of pH 6.8 phosphate buffer and a paddle speed of 50 rpm. Testing was performed over 22 h.

Potency results are summarised for the fluvoxamine 100 mg CR beads in Table 6. It is evident from this table that as the percentage polymer coat increases the potency decreases (the 4% coated beads had a potency of 464.8 mg/g compared to 295.9 mg/g for the 15% coated beads). This result obtained is expected as the potency values are calculated on the basis of actual potency of active per final weight of bead (mg/g).

TABLE 6

Potency Results for Fluvoxamine 100 mg CR Beads

| | Polymer Coat | | | | |
|---|---|---|---|---|---|
| % w/w | 4.0 | 8.0 | 10.0 | 12.0 | 15.0 |
| Potency (mg/g) | 464.8 | 386 | 353 | 329.6 | 295.9 |

The dissolution results are summarised in Table 7.

TABLE 7

Dissolution Results for Fluvoxamine 100 mg CR Beads

| % Coat | 4.0 | 6.0 | 8.0 | 10.0 | 12.0 | 15.0 |
|---|---|---|---|---|---|---|
| Time (h.) | | | % Released | | | |
| 0.5 | 4.3 | 2.2 | 2.7 | 0.8 | 1.0 | 1.1 |
| 1.0 | 15.6 | 2.8 | 3.2 | 1.7 | 1.8 | 1.9 |
| 2.0 | 62.3 | 8.4 | 5.3 | 2.0 | 1.7 | 1.5 |
| 4.0 | 93.2 | 48.7 | 6.6 | 2.1 | 1.8 | 1.7 |
| 6.0 | 96.5 | 83.2 | 26.2 | 6.5 | 3.4 | 2.5 |
| 8.0 | 98.4 | 92.9 | 59.8 | 23.2 | 4.1 | 2.4 |
| 10.0 | 97.6 | 96.3 | 78.3 | 41.8 | 11.3 | 2.7 |
| 22.0 | 100.1 | 100.8 | 96.5 | 98.8 | 83.3 | 56.2 |

Manufacture of Fluvoxamine Maleate 100 mg CR Capsules

White/White opaque size 2 gelatin capsules were dual-filled utilising the Bosch encapsulator (E5572). A batch size of 600 g was selected for all four products. The limits on the Bosch were set in order to fill the required percentage of each of the two types of controlled release beads. Tables 8A and 8B show the formulation details for fluvoxamine Maleate 100 mg CR capsules. The products are denoted as A, B, C and D.

TABLE 8A

Formulation Details For Fluvoxamine Maleate 100 mg CR Capsules.

| | Product No. | | | | | |
|---|---|---|---|---|---|---|
| | A | | | B | | |
| Composition | % | mg/capsule | Batch Size (Kg) | % | mg/Capsule | Batch Size (Kg) |
| 4% coated Fluvox.CR Beads | 100 | 215.15 | 0.600 | 60 | 129.0 | 0.360 |
| 6% coated Fluvox.CR Beads | — | — | — | 40 | 96.2 | 0.240 |
| 8% coated Fluvox.CR Beads | — | — | — | — | — | — |
| Total | 100 | 215.15 | 0.600 | 100 | 225.2 | 0.600 |

TABLE 8B

Formulation Details For Fluvoxamine Maleate 100 mg CR Capsules.

| | Product No. | | | | | |
|---|---|---|---|---|---|---|
| | C | | | D | | |
| Composition | % | mg/capsule | Batch Size (Kg) | % | mg/Capsule | Batch Size (Kg) |
| 4% coated Fluvox.CR Beads | 62 | 133.40 | 0.372 | 40 | 86.06 | 0.240 |
| 6% coated Fluvox.CR Beads | — | — | — | — | — | — |

TABLE 8B-continued

Formulation Details For Fluvoxamine Maleate 100 mg CR Capsules.

| | Product No. | | | | | |
|---|---|---|---|---|---|---|
| | C | | | D | | |
| Composition | % | mg/capsule | Batch Size (Kg) | % | mg/Capsule | Batch Size (Kg) |
| Fluvox.CR Beads 8% coated | 38 | 98.45 | 0.228 | 60 | 155.44 | 0.360 |
| Fluvox.CR Beads Total | 100 | 231.85 | 0.600 | 100 | 241.5 | 0.600 |

In order to obtain the required dissolution rates for three of the products two different levels of polymer coats were "blended" by dual filling.

Potency and dissolution testing were performed on the manufactured CR capsules. Dissolution testing was performed using USP Apparatus 2, with 900 ml of pH 6.8 phosphate buffer and a paddle speed of 50 rpm. Testing was performed over 22 h.

Table 9 summarises the potency results for the 100 mg capsules. Capsule manufacture was successful as all capsule batches had a potency value greater than 97%

TABLE 9

Potency Results for Fluvoxamine 100 mg CR Capsules

| Product No. | Actual Potency (mg/g) |
|---|---|
| A | 97.6 |
| B | 99.0 |
| C | 98.4 |
| D | 99.6 |

Table 10 shows the dissolution results for the 100 mg capsules. The results proved that dual filling was an acceptable method of "blending" the different levels of polymer coated beads. Also the combinations used were successful in that they reflected the predicted simulations.

TABLE 10

Dissolution Results for Fluvoxamine 100 mg CR Capsules.

| Product No. Time (h.) | A | B | C | D |
|---|---|---|---|---|
| | | % Released | | |
| 0.5 | 5.1 | 2.85 | 2.75 | 3.15 |
| 1.0 | 15.8 | 8.8 | 7.85 | 5.35 |
| 2.0 | 63.4 | 41.35 | 35.7 | 25.7 |
| 4.0 | 91.6 | 79.55 | 69.95 | 51.55 |
| 6.0 | 97.3 | 93.1 | 84.55 | 71.0 |
| 8.0 | 98.9 | 95.8 | 91.5 | 82.75 |
| 10.0 | 100.5 | 99.65 | 96.1 | 90.85 |
| 22.0 | 98.6 | 98.9 | 100.85 | 102.85 |

Example 2

Production of Further Controlled Release Capsules

Manufacture of Drug Loaded Beads

Drug loaded beads were prepared as described in Example 1 except that the beads were oven dried at 55° C. for 18 h. Sieving was carried out on screen sizes 0.98 mm and 1.5 mm. The formulation details are set out in Table 11.

TABLE 11

Formulation details for Fluvoxamine Loaded Beads

| Batch No.<br>Composition | 3<br>(Kg) | 4<br>(Kg) |
|---|---|---|
| Fluvoxamine Maleate | 12.450 | 12.450 |
| Talc | 3.550 | 3.550 |
| (% of active) | 28.5% | 28.5% |
| Total | 16.000 | 16.000 |
| Non-Pareil Seeds | 5.000<br>(0.71-0.85 mm) | 5.000<br>(0.71-0.85 mm) |
| Eudragit RS (12.5%<br>Polymer Solids) | 1.316 | 1.413 |

The drug loaded beads produced were evaluated for potency and dissolution.

Dissolution testing was conducted on USP Apparatus 2, using 900 ml of pH 6.8 phosphate buffer and a paddle speed of 50 rpm. All testing, by UV detection was replicated by six.

Table 12 details the potency results. Based on the potency results, a drug loading of 54% was achieved using the 0.71-0.85 mm non-pareil seeds. The potency and dissolution results of the previous IR and CR batches from Example 1 (Batch 1 and Batch 2 respectively) are included as beads from these batches were used to make capsules.

TABLE 12

Potency Results for Fluvoxamine Maleate Drug Loaded Beads

| Batch No. | Actual Potency (mg/g) |
|---|---|
| 3 | 537.1 |
| 4 | 530.1 |

Table 13 and FIG. 1 summarise the dissolution results. The results satisfy the USP specifications for immediate release (IR) products of ≧75% released in 45 min. (e.g. Batch: 3 95.4% released after 45 min.; Batch 4: 99.1% released after 45 min.).

TABLE 13

Dissolution Results for Fluvoxamine Maleate Drug Loaded Beads

| Batch No.<br>Time (min.) | 3 | 4 |
|---|---|---|
| | % Released | |
| 15 | 84.6 | 88.7 |
| 18 | N/A | N/A |
| 30 | 93.8 | 96.1 |
| 45 | 95.4 | 99.1 |
| 48 | N/A | N/A |
| 60 | 96.5 | 99.7 |
| 120 | 97.8 | 101.6 |

Manufacture of Controlled Release Beads

Controlled release beads were produced by the polymeric coating of the drug-loaded beads. The polymer coating solution and talc were applied simultaneously at controlled rates. The application of talc at this stage prevents agglomeration of the beads during the coating process.

The IR batch was coated with an Eudragit RS plus dibutyl sebecate coating solution (coating solution contained 7.4% solids: polymer+plasticiser).

During the process, beads were sampled at 4%, 6%, 8%, 12% and 15% levels of polymer coat. Table 14 gives formulation details for the batch produced. Table 15 summarises the coating polymer formulation details for the fluvoxamine 100 mg CR beads. The controlled release beads were manufactured in accordance with the procedure set forth in Example 1, but without a sieving step.

TABLE 14

Formulation Details For Fluvoxamine Maleate CR Beads

| Batch No. | 5 | 6 |
|---|---|---|
| Input Drug Loaded Bead | 4 | 3 |
| Composition | Kg | Kg |
| Fluvoxamine IR Beads | 15.000 | 15.000 |
| Talc | 9.0669 | 7.909 |
| (% of polymer solids) | (504.0) | (386) |
| Eudragit RS + DBS | 29.1265 | 27.693 |
| Coating solution | (PD15349) | (PD15482) |
| (6.17% polymer solids) | (1.797) | (2.049) |

TABLE 15

Formulation Details of Polymer Used in the Manufacture of Fluvoxamine Maleate CR Beads.

| Coating Solution<br>Composition | Eudragit RS + Plasticiser<br>(Kg) |
|---|---|
| Eudragit RS (12.5) | 18.000 |
| I.P.A. | 18.000 |
| DBS | 0.450 |
| TOTAL | 36.450 |

Potency and Dissolution testing were performed on the manufactured controlled release beads (i.e. 4%, 6%, 8%, 12% and 15%). Dissolution testing was performed using USP Apparatus 2, with 900 mls of pH 6.8 phosphate buffer and a paddle speed of 50 rpm. Testing was performed over 22 h.

Potency results are summarised for the fluvoxamine 100 mg CR beads in Tables 16 and 17.

TABLE 16

Potency Results for Fluvoxamine Maleate CR Beads

| | Polymer Coat | | | | |
|---|---|---|---|---|---|
| Batch No. | 5<br>4.0% | 6<br>6.0% | 7<br>8.0% | 8<br>12.0% | 9<br>15.0% |
| Potency (mg/g) | 441.9 | 406.9 | 375.9 | 326.5 | 290.5 |

TABLE 17

Potency Results for Fluvoxamine Maleate CR Beads Produced in Example 1

| | Polymer Coat | | | | | |
|---|---|---|---|---|---|---|
| | 4.0% | 6.0% | 8.0% | 10.0% | 12.0% | 15.0% |
| Potency (mg/g) | 464.8 | 415.8 | 386 | 353 | 329.6 | 295.9 |

On comparison of the values with the potency values for the batch of Example 1a difference was observed particularly at the 4% level (i.e. Example 1: 4%=464.8 mg/g).

The dissolution results are summarised in Tables 18 and 19. As expected, as the level of coat increases, the lag time is increased and a much slower dissolution profile results.

TABLE 18

Dissolution Results for Fluvoxamine Maleate CR Beads (RS. + DBS Coat)

| Batch No. | 5 | 6 | 7 | 8 | 9 |
|---|---|---|---|---|---|
| % Coat | 4.0 | 6.0 | 8.0 | 12.0 | 15.0 |
| Time (h.) | | % Drug Released | | | |
| 0.5 | 3.5 | 2.4 | 1.6 | 1.8 | 2.0 |
| 1.0 | 14.1 | 2.9 | 1.6 | 1.4 | 1.5 |
| 2.0 | 67.9 | 6.1 | 1.8 | 2.1 | 2.2 |
| 4.0 | 92.5 | 65.4 | 10.2 | 2.0 | 1.5 |
| 6.0 | 96.8 | 88.9 | 54.2 | 3.3 | 1.7 |
| 8.0 | 102.4 | 99.7 | 80.2 | 6.8 | 1.0 |
| 10.0 | 104.3 | 103.8 | 91.4 | 23.2 | 1.9 |
| 22.0 | 98.2 | 97.2 | 99.3 | 96.0 | 79.0 |

TABLE 19

Dissolution Results for Fluvoxamine Maleate CR Beads from Example 1

| % Coat | 4.0 | 6.0 | 8.0 | 10.0 | 12.0 | 15.0 |
|---|---|---|---|---|---|---|
| Time (h.) | | | % Drug Released | | | |
| 0.5 | 4.3 | 2.2 | 2.7 | 0.8 | 1.0 | 1.1 |
| 1.0 | 15.6 | 2.8 | 3.2 | 1.7 | 1.8 | 1.9 |
| 2.0 | 62.3 | 8.4 | 5.3 | 2.0 | 1.7 | 1.5 |
| 4.0 | 93.2 | 48.7 | 6.6 | 2.1 | 1.8 | 1.7 |
| 6.0 | 96.5 | 83.2 | 26.2 | 6.5 | 3.4 | 2.5 |
| 8.0 | 98.4 | 92.9 | 59.8 | 23.2 | 4.1 | 2.4 |
| 10.0 | 97.6 | 96.3 | 78.3 | 41.8 | 11.3 | 2.7 |
| 22.0 | 100.1 | 100.8 | 96.5 | 98.8 | 83.3 | 56.2 |

It was expected that the 8% polymer coated batches would have given similar dissolution results since Batch 5 was intended to be a similar batch to the batch of Example 1. The differences can be explained by the slight differences in processing. The product of Example 1 gave a more desirable dissolution profile.

Manufacture of Fluvoxamine Maleate 100 mg CR Capsules

White/White opaque size 2 gelatin capsules were dual-filled utilising the Bosch encapsulator (E5572). A batch size of 0.4789 Kg was selected for Product C and 0.4919 Kg for Product D. The limits on the Bosch were set in order to fill the required percentage of each of the two types of controlled release beads. Table 20 shows the formulation details for fluvoxamine maleate 100 mg CR capsules.

TABLE 20

Formulation Details For Fluvoxamine Maleate 100 mg CR Capsules.

| | | Batch No. | | | | |
|---|---|---|---|---|---|---|
| | | 10 | | | 11 | |
| Composition | % | mg/ capsule | Batch Size (Kg) | % | mg/ Capsule | Batch Size (Kg) |
| 4% coated Fluvox.CR Beads | 60 | 135.8 | 0.2716 | 40 | 90.5 | 0.1810 |
| 8% coated Fluvox.CR Beads | 40 | 103.6 | 0.2073 | 60 | 155.4 | 0.3109 |
| Total | 100 | 239.4 | 0.4789 | 100 | 245.9 | 0.4919 |

The Food Effect and Steady State studies the subject of Example 4 and Example 5 and 6, respectively required 100 mg CR capsules with a similar release profile to Product C and Product D capsules that were included in the biostudy of Example 3. In order to achieve this it was considered appropriate to use the Example 1, 8% beads and the Batch 5, 4% beads of the present Example.

In order to maintain, some consistency it was decided to adhere to the combination ratio 40% of 4% and 60% of 8% for Product D and the Product C combination was altered to the more rounded figures of 60% of 4% and 40% of 8%.

Potency and dissolution testing were performed on the manufactured CR capsules. Dissolution testing was performed using USP Apparatus 2, with 900 ml of pH 6.8 phosphate buffer and a paddle speed of 50 rpm. Testing was performed over 22 hours.

Table 21 summarises the potency results for the 100 mg capsules.

TABLE 21

Potency Results for Fluvoxamine 100 mg CR Capsules

| Batch No. | Actual Potency (mg/g) |
|---|---|
| 10 | 97.3 |
| 11 | 96.2 |

The dissolution results were very similar to the results of Product C and Product D capsules obtained in Example 1.

The new capsule batches showed slightly faster dissolution rates as shown in Table 22 and FIG. 1.

In FIG. 1 curve a corresponds to Batch No. 10 and curve b corresponds to Batch No. 11.

TABLE 22

Dissolution Results for Fluvoxamine 100 mg CR Capsules.

| Batch No. | 10 | 11 |
|---|---|---|
| Time (h.) | % Released | |
| 0.5 | 2.76 | 4.78 |
| 1.0 | 9.04 | 10.26 |
| 2.0 | 45.99 | 35.45 |
| 4.0 | 74.23 | 58.88 |
| 6.0 | 85.62 | 75.42 |
| 8.0 | 92.76 | 86.48 |
| 10.0 | 96.57 | 92.24 |
| 22.0 | 100.36 | 100.80 |

Example 3

Biostudy

A biostudy was carried out with the primary objective of comparing the relative bioavailability of the 100 mg capsule formulations A-D (Products A-D) referred to in Examples 1 and 2 relative to Luvox® 100 mg tablets (Solvay Pharmaceuticals Inc.). A secondary objective was to characterize the plasma concentration profile of the CR formulation relative to Luvox® 100 mg tablets.

The biostudy had an open label, single dose, five treatment, five period, randomised, crossover design with at least a ten day washout period between treatment days.

Non-compartmental pharmacokinetic assessment was based on the plasma levels of fluvoxamine measured by blood sampling. Blood samples were obtained before dosing and at the following times after administration of both the reference and test medications: 0 (predose), 1, 2, 3, 4, 5, 6, 7, 8, 9, 10, 12, 14, 16, 20, 24, 30, 36, 48, 72 and 96 hours.

Ten (10) subjects were enrolled and completed the study. All 10 subjects were included in the pharmacokinetic and safety analyses.

Diagnosis and Main Criteria for Inclusion:

Healthy male subjects aged between 18 and 40 years, who were phenotyped as extensive metabolisers of dextromethorphan.

Test Product, Dose and Mode of Administration:

Fluvoxamine 100 mg CR capsule—Product A (very fast dissolution)

Fluvoxamine 100 mg CR capsule—Product B (fast dissolution)

Fluvoxamine 100 mg CR capsule—Product C (medium dissolution)

Fluvoxamine 100 mg CR capsule—Product D (slow dissolution)

Subjects received a single oral dose of one capsule with 240 ml of tap water following a 10 hour fast.

Reference Product, Dose and Mode of Administration:

Luvox® 100 mg Tablet (Product E)

Subjects received a single oral dose of one tablet with 240 ml of tap water following a 10 h. fast.

Pharmacokinetics: The following pharmacokinetic parameters were calculated using non-compartmental methods: the area under the drug plasma concentration curve from the time of dosing to the time of the last sampling point (AUC(0-t); the area under the drug plasma concentration versus time curve extrapolated to infinity (AUC(0-∞)); the maximum measured concentration of the drug in the plasma (Cmax) and the time at which this concentration was measured (tmax); the concentration at 24 hours (C24 h); the relative bioavailability of the test(s) compared to the reference product (Frel(%)); the time taken for the drug plasma concentration to decrease by 50% (t½); and the terminal first-order elimination rate constant (Kel).

Statistical Methods:

Descriptive statistics of relevant pharmacokinetic parameters were performed. An analysis of variance (ANOVA) was used to assess treatment differences.

Figure 2:
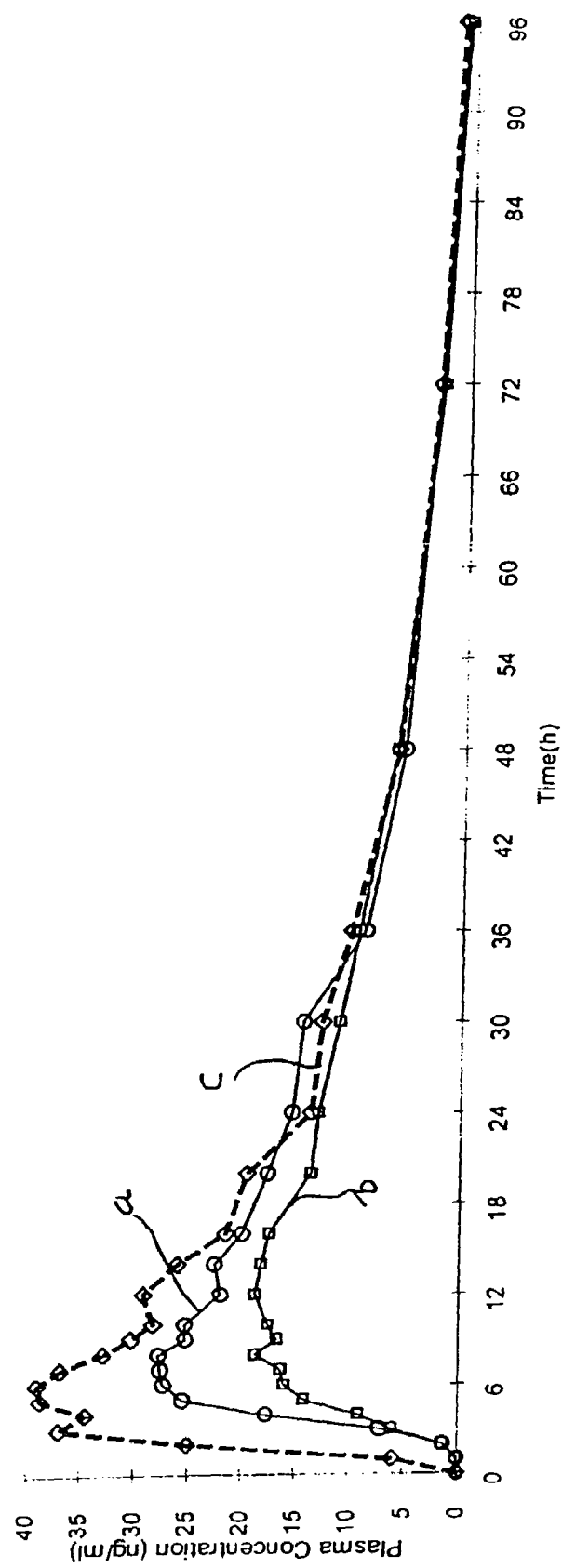
FIG. 2 is a plot of plasma fluvoxamine concentration (ng/ml) after single dose administration for a number of formulations prepared according to the invention versus time (h) compared with the plasma profile for tablets as sold under the Trade Mark Luvox as described in Example 3.

Pharmacokinetic Results:

A summary of the statistical analysis and confidence intervals of the pharmacokinetic parameters is contained in Table 23. The mean plasma concentration versus time curve is depicted in FIG. 2 wherein curve a represents Product C, curve b represents Product D and curve c represents the reference Luvox®

TABLE 23

Summary statistics and confidence intervals for non-transformed pharmacokinetic parameters

| Parameter | Product A Mean ± St dev | Product B Mean ± St dev | Product C Mean ± St dev | Product D Mean ± St dev | Luvox® Mean ± St dev |
|---|---|---|---|---|---|
| AUC (0-∞) (ng/ml.h) | 919.960 ± 747.132 | 1014.213 ± 885.705 | 872.731 ± 688.717 | 725.457 ± 450.549 | 1047.194 ± 959.337 |
| Frel(%) | 95.201 ± 31.844 | 101.486 ± 24.936 | 91.152 ± 25.714 | 83.053 ± 34.432 | — |
| Cmax (ng/ml) | 40.514 ± 16491 | 40.611 ± 17.973 | 31.361 ± 15.035 | 22.711 ± 9.146 | 44.576 ± 23.132 |
| tmax(h) | 5.600 ± 0.843 | 6.900 ± 2.025 | 6.900 ± 1.663 | 12.400 ± 5.296* | 4.200 ± 1.614 |
| C24h (ng/ml) | 13.79 ± 9.45 | 15.95 ± 14.03 | 15.57 ± 11.92 | 13.09 ± 7.49 | 13.73 ± 13.03 |

Conclusion:

All of the formulations according to the invention tested had reduced Cmax compared to that of the reference product (Luvox® tablets), with Products C and D being significantly reduced. The tmax of all of the formulations according to the invention were prolonged relative to that of Luvox® tablets. The tmax of Product D was significantly extended. The relative bioavailabilities of the all formulations were ≧80% relative to Luvox® tablets.

Example 4

Determination of the Effect of Food on the Relative Bioavailability of a Fluvoxamine Controlled Release Formulation The study was carried out to assess the effect of food on the relative bioavailability of Product C prepared in Example 2.

Methodology:

The study had an open label, single dose, two-treatment, two-period, randomised, crossover design with a 10-day washout period between treatment periods. Non-compartmental pharmacokinetic assessment was based on the plasma levels of fluvoxamine. Blood samples were obtained before dosing and at the following times after administration of both the reference and test medications: 0 (predose), 1, 2, 3, 4, 5, 6, 7, 8, 9, 10, 12, 14, 16, 20, 24, 30, 36, 48, 72 and 96 hours postdose.

Number of Subjects (Planned and Analysed):

A total of 16 subjects, 13 males and 3 females, with a mean age of 27.3 years, were enrolled in the study. Subject 9 discontinued the study due to personal reasons after completing the 72 hour pharmacokinetic blood draw of Period 2. All 16 subjects were included in the pharmacokinetic analyses.

Diagnosis and Main Criteria for Inclusion:

Healthy male and female subjects aged between 18 and 45 years who were phenotyped as extensive metabolisers of dextromethorphan.

Test Product, Dose and Mode of Administration:

Subjects received a single oral dose of Product C with 180 ml of tap water either following an overnight fast of 10 h. or following a high fat meal.

Pharmacokinetics

The following pharmacokinetic parameters were calculated using non-compartmental methods: the area under the plasma concentration-time curve from the time of dosing to the time of the last sampling point [AUC(0-t)]; the area under the plasma concentration versus time curve extrapolated to infinity AUC(0-∞); the maximum measured concentration of the drug in the plasma (Cmax) and the time at which this concentration was measured (tmax); the relative bioavailability, F, of the formulation under fasted and fed conditions; the time required for the drug plasma concentration to decrease by 50% (t½); and the terminal first-order elimination rate constant (Kel).

Statistical Methods

Non-compartmental pharmacokinetic parameters were calculated and descriptive statistics were performed. An analysis of variance (ANOVA) was used to assess treatment differences.

Figure 3:
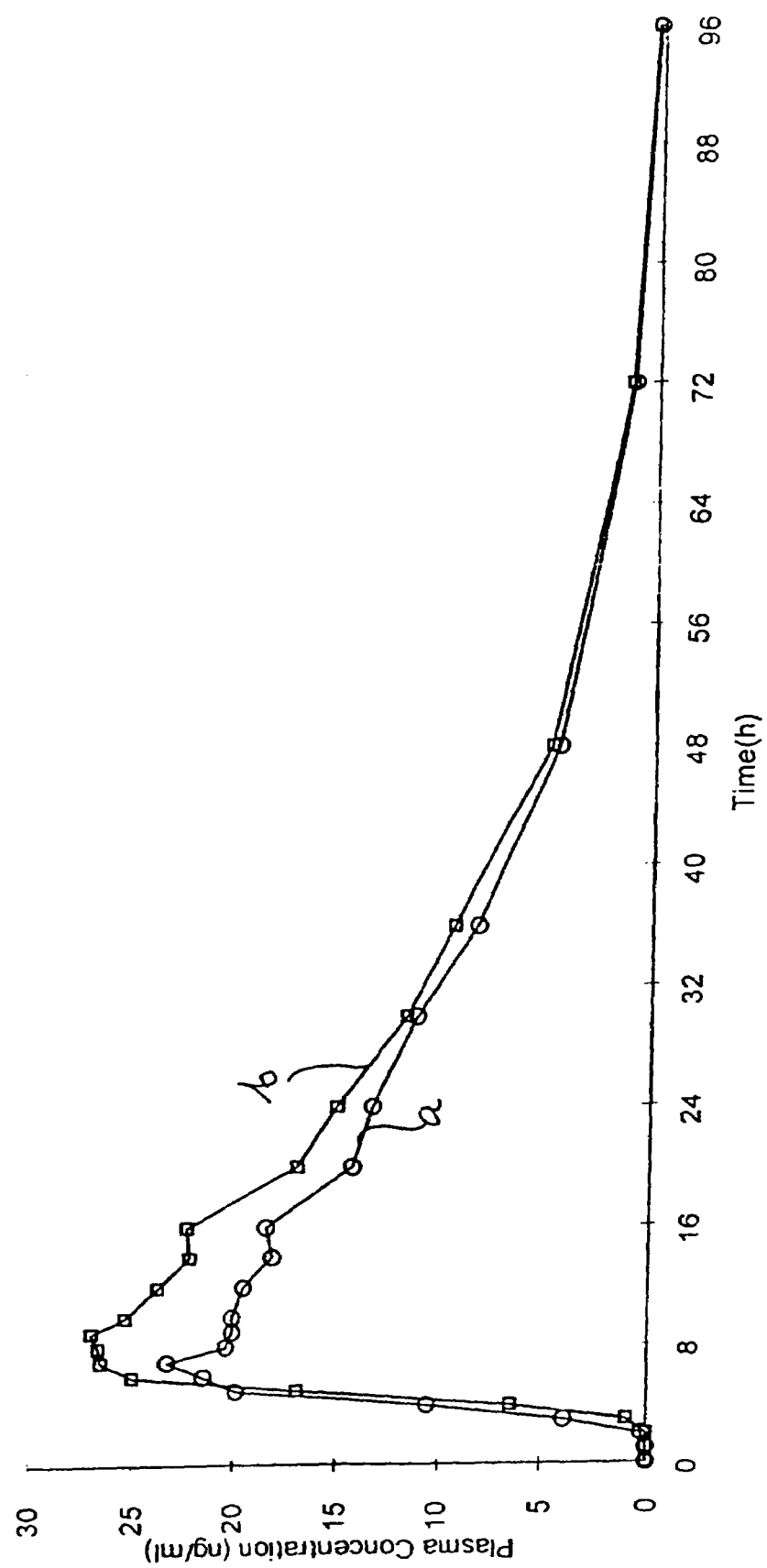
FIG. 3 is a plot of plasma fluvoxamine concentration (ng/ml) versus time (h) under fasted and fed conditions as described in Example 4.

Pharmacokinetics Results:

The pharmacokinetic results are summarized in Table 24 and in FIG. 3. In FIG. 3 curve a represents fasted conditions and curve b represents fed conditions.

TABLE 24

Mean (SD) Plasma Pharmacokinetic Parameters After Single Dose Administration of Product C Under Fasted or Fed Conditions

| N = 16 Subjects | Product C Fasted | Product C Fed |
|---|---|---|
| Cmax (ng/ml) | 26.63 (8.15) | 31.45 (12.79) |
| tmax (h) | 7.13 (2.66) | 8.00 (2.07) |
| AUC(0-∞) (ng · hr/ml) | 667.43 (328.07) | 760.03 (319.43) |

The mean Cmax and AUC(0-∞) of fluvoxamine were increased in the presence of food by 18% and 14%, respectively. This increase was not considered to be of any clinical significance. There was no evidence of dose dumping of the CR formulation in the presence of food.

Conclusion:

Both treatments appeared to be safe and well tolerated in this population. No clinically significant interaction with food was observed for the CR formulation.

Example 5

Determination of the Pharmacokinetics of Fluvoxamine After Multiple Doses of a Fluvoxamine CR 100 mg Capsule and a 100 mg Luvox® Tablet in Healthy Male Volunteers A study was carried out to determine the pharmacokinetics of fluvoxamine after multiple doses of product C prepared in Example 2 and 100 mg Luvox® in healthy male volunteers.

Methodology:

Multiple-dose, open-label, two-treatment, two-period, balanced, randomized, crossover study with a seven-day washout between the last dose of fluvoxamine in Period 1 and the first dose of fluvoxamine in Period 2.

Number of Subjects (Planned and Analyzed):

Twelve (12) subjects, with a mean age of 26.3 years, were enrolled and ten completed the study. Two subjects withdrew for reasons unrelated to the study medication. The 10 completed subjects were included in the pharmacokinetic analysis.

Diagnosis and Main Criteria for Inclusion:

Healthy male volunteers, aged 18 and 45 years inclusive, who were phenotyped as extensive metabolisers of dextromethorphan.

Test Product, Dose and Mode of Administration:

Product C

Each subject received a single oral dose taken with 180 ml of tap water once daily for 10 consecutive days during each treatment period.

Reference Product, Dose and Mode of Administration:

Luvox® (fluvoxamine maleate) 100 mg Tablet

Each subject received a single oral dose taken with 180 ml of tap water once daily for 10 consecutive days during each treatment period.

Pharmacokinetics:

Blood samples were obtained at the following times relative to administration of both the Reference and Test treatments on Days 10 and 27.

1, 2, 3, 4, 5, 6, 7, 8, 9, 10, 12, 14, 16, 20, 24, 30, 36, and 48 h.

In addition, predose blood samples were collected on the mornings of Days 1 to 10 and 18 to 27 prior to drug administration.

The following pharmacokinetic parameters were determined for fluvoxamine after each treatment using non-compartmental methods:

The area under the plasma concentration-time curve within a 24-hour dosing interval after multiple dosing AUC (0-τ).

The maximum plasma concentration of the drug, Cmax, and the time of its occurrence, tmax.

Time required to achieve steady-state conditions.

The minimum plasma concentration, Cmin.

The mean plasma concentration within a dosing interval, Cav.

The relative bioavailability, F, of Product C compared to Luvox® tablets, as defined by ratio of AUC(0-τ).

The peak to trough fluctuation, PTF, defined as (Cmax−Cmin)/Cav.

Statistical Methods:

Descriptive statistics were provided for assessment of pharmacokinetic parameters obtained between the two fluvoxamine treatments. The minimum plasma concentrations of fluvoxamine were compared within each treatment period to determine if steady-state conditions had been achieved after 10 consecutive administrations.

Figure 4:
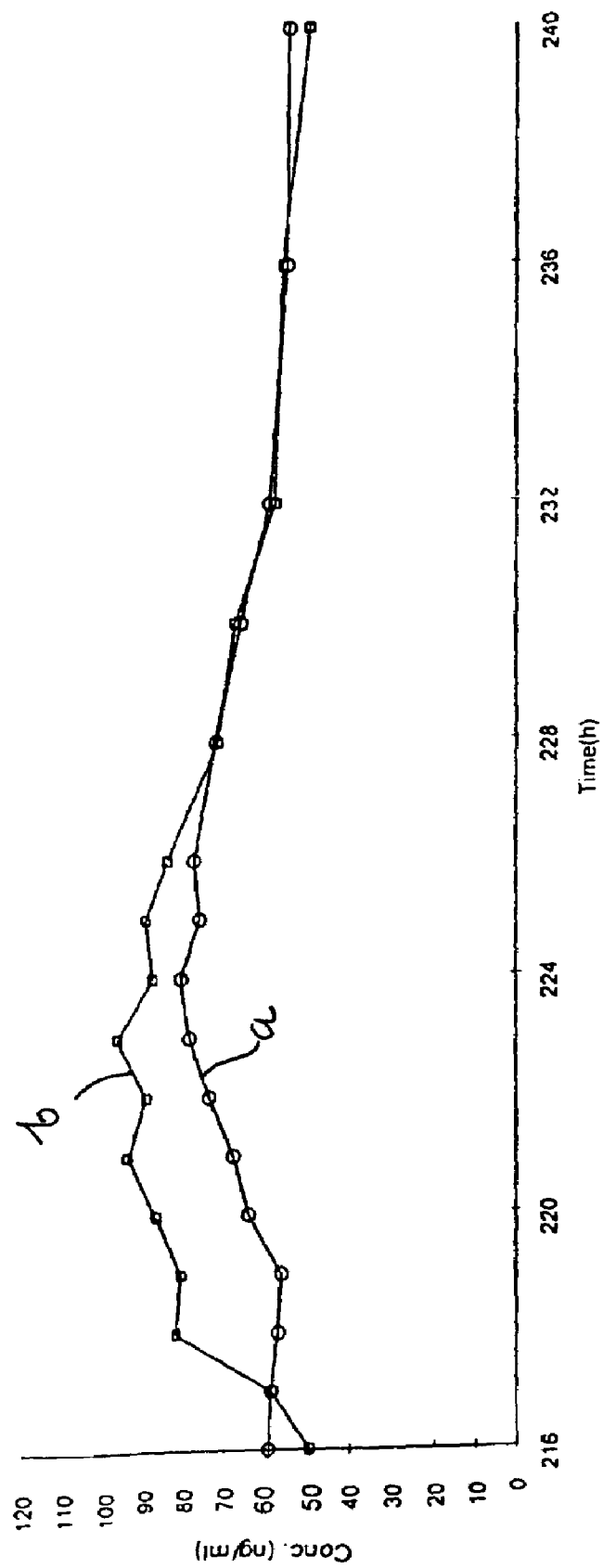
FIG. 4 is a plot of plasma fluvoxamine concentration (ng/ml) under steady state conditions for Product C as prepared in Example 1 verus time (h) compared with the plasma profile for tablets as sold under the Trade Mark Luvox as described in Example 5.

Pharmacokinetics Results:

Pharmacokinetic results are summarized in Table 25 and FIG. 4: In FIG. 4 curve a represents product C and curve b represents the reference Luvox®

TABLE 25

Mean (SD) Multiple-Dose Plasma Pharmacokinetic Parameters After Once Daily Administration of 100 mg Fluvoxamine Maleate for 10 Days in the Form of Either Product C or Luvox ® Tablets

| N = 10 Males | Product C | Luvox ® Tablets |
|---|---|---|
| Cmax | 91.85 | 107.00 |
| (ng/ml) | (63.67) | (73.52) |
| tmax | 8.90 | 6.80 |
| (h.) | (1.97) | (2.15) |
| Cmin | 44.51 | 43.76 |
| (ng/ml) | (34.78) | (41.15) |
| AUC(0-τ) | 1543.18 | 1738.55 |
| (ng · h/ml) | (1136.99) | (1392.42) |
| Fluctuation Index | 0.85 (0.22) | 1.13 (0.38) |

The relative bioavailability Product C compared with Luvox® tablets based on AUC(0-τ) was 94.0%. Product C also showed a smaller fluctuation index, reflecting lower Cmax values compared with Luvox® tablets.

Conclusion:

Both treatments were safe and well tolerated in this healthy male population. Product C performed comparably to Luvox® tablets after multiple doses and exhibited less fluctuation in plasma concentrations of fluvoxamine.

Example 6

Determination of the Pharmacokinetics of Fluvoxamine After Multiple Doses of a Fluvoxamine CR 100 mg Capsule and a 100 mg Luvox® Tablet in Healthy Male Volunteers A study was carried out to determine the pharmacokinetics of fluvoxamine after multiple doses of product D referred to in Example 1 and 100 mg Luvox® in healthy male volunteers.

Methodology:

Multiple-dose, open-label, two-treatment, two-period, balanced, randomized, crossover study with a seven-day washout between the last of fluvoxamine in Period 1 and the first dose of fluvoxamine in Period 2.

Number of Subjects (Planned and Analyzed):

A total of fourteen (14) subjects, with a mean age of 31.1 years, were enrolled. All 14 subjects completed the study and were included in the pharmacokinetic analyses.

Diagnosis and Main Criteria for Inclusion:

Healthy male subjects aged between 18 and 45 years, who were phenotyped as extensive metabolisers of dextromethorphan.

Test Product, Dose and Mode of Administration:

Product D

Each subject received a single oral dose taken with 180 ml of tap water once daily for 10 consecutive days during each treatment period.

Reference Product, Dose and Mode of Administration:

Luvox® (fluvoxamine maleate) 100 mg tablets.

Each subject received a single oral dose taken with 180 ml of tap water once daily for 10 consecutive days during each treatment period.

Pharmacokinetics:

The same procedure was adopted as in the case of Example 4.

Statistical Methods:

The same format was adopted as in the case of Example 4.

Figure 5:
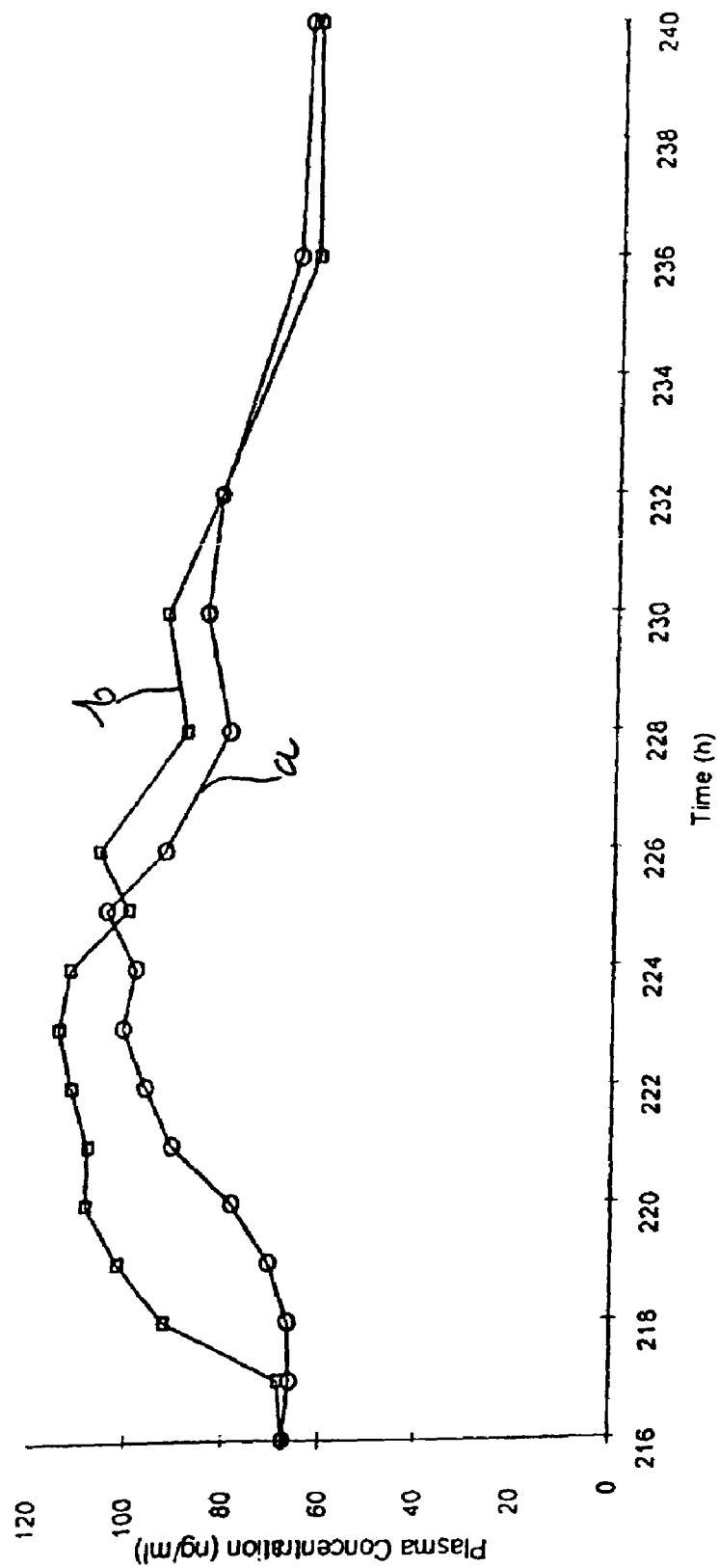
FIG. 5 is a plot of plasma fluvoxamine concentration (ng/ml) under steady state conditions for Product D as prepared in Example 1 verus time (h) compared with the plasma profile for tablets as sold under the Trade Mark Luvox as described in Example 6.

Pharmacokinetics Results:

The pharmacokinetic results are summarized in Table 26 and FIG. 5. In FIG. 5 curve a represents Product D and curve b represents the reference Luvox®.

TABLE 26

Mean (SD) Multiple-Dose Plasma Pharmacokinetic Parameters After Once Daily Administration of 100 mg Fluvoxamine Maleate for Ten Days in the Form of Either Product D or Luvox ® Tablets

| N = 14 Males | Product D | Luvox ® Tablets |
|---|---|---|
| Cmax | 114.87 | 129.59 |
| (ng/ml) | (58.09) | (62.86) |
| tmax | 7.79 | 6.43 |
| (h.) | (1.19) | (2.24) |
| cmin | 57.41 | 54.56 |
| (ng/ml) | (34.39) | (32.69) |
| AUC(0-τ) | 1929.09 | 2109.30 |
| (ng · hr/ml) | (1048.27) | (1085.63) |
| Fluctuation Index | 0.77 (0.27) | 0.91 (0.19) |

The relative bioavailability of Product D compared with Luvox® tablets based on AUC(0-τ) was 91.0%. Product D also showed a smaller fluctuation index, reflecting lower Cmax values compared with Luvox® tablets.

Conclusion:

Both treatments were safe and well tolerated in this healthy male population. The CR formulation performed comparably to Luvox® tablets after multiple doses and exhibited less fluctuation in plasma concentrations of fluvoxamine.

The invention claimed is:

1. A multiparticulate controlled release selective serotonin reuptake inhibitor (SSRI) composition for oral administration comprising two quantities of particles, each of the particles comprising
   (i) an inert non-pareil core,
   (ii) an SSRI layer comprising fluvoxamine or a pharmaceutically-acceptable salt thereof disposed over the inert core, and
   (iii) a coating of a rate-controlling polymeric acrylate, methacrylate lacquer, or a mixture thereof disposed over the fluvoxamine,
   wherein the composition allows the controlled release of the fluvoxamine over a period of not less than about 12 hours following oral administration, wherein the rate-controlling polymeric acrylate or methacrylate lacquer coating of the first quantity of particles is present in a first amount, and the rate-controlling polymeric acrylate or methacrylate lacquer coating of the second quantity of particles is present in a second amount that is different from the first amount, and wherein the fluvoxamine release rate from the composition exhibits the following in vitro dissolution pattern when measured using a USP type II dissolution apparatus (paddle) according to US Pharmacopeia XXII in 0.05 M phosphate buffer at pH 6.8:
   (a) no more than about 15% of the total fluvoxamine is released after 0.5 of an hour of measurement in the apparatus;

(b) no more than about 25% of the total fluvoxamine is released after 1 hour of measurement in the apparatus;

(c) between about 20% and 75% of the total fluvoxamine is released after 2 hours of measurement in the apparatus;

(d) not less than about 75% of the total fluvoxamine is released after 4 hours of measurement in the apparatus; and (e) not less than about 85% of the total fluvoxamine is released after 6 hours of measurement in the apparatus.

2. The composition according to claim 1 wherein the coating is the polymeric acrylate lacquer.

3. The composition according to claim 1 wherein the coating is the methacrylate lacquer.

4. The composition according to claim 1 wherein the coating is a lacquer which contains a mixture of acrylate and methacrylate.

5. The composition according to claim 1 wherein the coating is an acrylic resin comprising a copolymer of acrylic and methacrylic acid esters having a low content of quaternary ammonium groups.

6. The composition of claim 1 wherein the rate-controlling coating comprises an ammonio methacrylate lacquer and a plasticizer, the combined amount of the ammonio methacrylate lacquer and the plasticizer in the membrane coating being in an amount of from about 4% to about 15% of the weight of the particle.

7. The composition of claim 6 wherein the combined amount of the ammonio methacrylate lacquer and the plasticizer in the rate controlling coating of the first or second quantity of particles is in an amount of 4%, 6%, 8%, 10%, 12%, or 15% of the weight of the particle.

8. The composition of claim 1, wherein the controlled-release of the fluvoxamine is effective in supplying fluvoxamine to the blood of a patient such that, following a single application of the composition to the patient, the amount of circulating fluvoxamine ($AUC_{0-\infty}$) in the blood serum of the patient is about 128 to about 1,175 ng/ml.h.

9. A multiparticulate controlled release selective serotonin reuptake inhibitor (SSRI) composition for oral administration comprising two quantities of particles, each of the particles comprising (i) an inert non-pareil core, (ii) an SSRI layer comprising fluvoxamine or a pharmaceutically-acceptable salt thereof disposed over the inert core, and (iii) a coating of a rate-controlling polymeric acrylate, methacrylate lacquer, or a mixture thereof disposed over the fluvoxamine, wherein the composition allows the controlled release of the fluvoxamine over a period of not less than about 12 hours following oral administration, wherein the rate-controlling polymeric acrylate or methacrylate lacquer coating of the first quantity of particles is present in a first amount, and the rate-controlling polymeric acrylate or methacrylate lacquer coating of the second quantity of particles is present in a second amount that is different from the first amount, and wherein the fluvoxamine release rate from the composition exhibits the following in vitro dissolution pattern when measured using a USP type II dissolution apparatus (paddle) according to US Pharmacopeia XXII in 0.05 M phosphate buffer at pH 6.8:

(a) no more than about 20% of the total fluvoxamine is released after 4 hours of measurement in the apparatus;

(b) no more than about 45% of the total fluvoxamine is released after 6 hours of measurement in the apparatus;

(c) between about 45% and 80% of the total fluvoxamine is released after 8 hours of measurement in the apparatus;

(d) not less than about 70% of the total fluvoxamine is released after 10 hours of measurement in the apparatus; and (e) not less than about 80% of the total fluvoxamine is released after 12 hours of measurement in the apparatus.

10. The composition of claim 9, wherein the coating is the polymeric acrylate lacquer.

11. The composition of claim 9, wherein the coating is the methacrylate lacquer.

12. The composition of claim 9, wherein the coating is a lacquer which contains a mixture of acrylate and methacrylate.

13. The composition of claim 9, wherein the coating is an acrylic resin comprising a copolymer of acrylic and methacrylic acid esters having a low content of quaternary ammonium groups.

14. The composition of claim 9, wherein the rate-controlling coating comprises an ammonio methacrylate lacquer and a plasticizer, the combined amount of the ammonio methacrylate lacquer and the plasticizer in the membrane coating being in an amount of from about 4% to about 15% of the weight of the particle.

15. The composition of claim 14, wherein the combined amount of the ammonio methacrylate lacquer and the plasticizer in the rate controlling coating of the first or second quantity of particles is in an amount of 4%, 6%, 8%, 10%, 12%, or 15% of the weight of the particle.

16. The composition of claim 9, wherein the controlled-release of the fluvoxamine is effective in supplying fluvoxamine to the blood of a patient such that, following a single application of the composition to the patient, the amount of circulating fluvoxamine ($AUC_{0-\infty}$) in the blood serum of the patient is about 128 to about 1,175 ng/ml.h.

17. A multiparticulate controlled release selective serotonin reuptake inhibitor (SSRI) composition for oral administration comprising two quantities of particles, each of the particles comprising (i) an inert non-pareil core, (ii) an SSRI layer comprising fluvoxamine or a pharmaceutically-acceptable salt thereof disposed over the inert core, and (iii) a coating of a rate-controlling polymeric acrylate, methacrylate lacquer, or a mixture thereof disposed over the fluvoxamine, wherein the composition allows the controlled release of the fluvoxamine over a period of not less than about 12 hours following oral administration, wherein the rate-controlling polymeric acrylate or methacrylate lacquer coating of the first quantity of particles is present in a first amount, and the rate-controlling polymeric acrylate or methacrylate lacquer coating of the second quantity of particles is present in a second amount that is different from the first amount, and wherein the fluvoxamine release rate from the composition exhibits the following in vitro dissolution pattern when measured using a USP type II dissolution apparatus (paddle) according to US Pharmacopeia XXII in 0.05 M phosphate buffer at pH 6.8:

(a) no more than 20% of the total fluvoxamine is released after 1 hour of measurement in the apparatus;

(b) no more than 60% of the total fluvoxamine is released after 2 hours of measurement in the apparatus;

(c) not less than 20% of the total fluvoxamine is released after 4 hours of measurement in the apparatus;

(d) not less than 35% of the total fluvoxamine is released after 6 hours of measurement in the apparatus;
(e) not less than 50% of the total fluvoxamine is released after 8 hours of measurement in the apparatus;
(f) not less than 70% of the total fluvoxamine is released after 10 hours of measurement in the apparatus; and
(g) not less than 75% of the total fluvoxamine is released after 12 hours of measurement in the apparatus.

18. The composition of claim 17, wherein the coating is the polymeric acrylate lacquer.

19. The composition of claim 17, wherein the coating is the methacrylate lacquer.

20. The composition of claim 17, wherein the coating is a lacquer which contains a mixture of acrylate and methacrylate.

21. The composition of claim 17, wherein the coating is an acrylic resin comprising a copolymer of acrylic and methacrylic acid esters having a low content of quaternary ammonium groups.

22. The composition of claim 17, wherein the rate-controlling coating comprises an ammonio methacrylate lacquer and a plasticizer, the combined amount of the ammonio methacrylate lacquer and the plasticizer in the membrane coating being in an amount of from about 4% to about 15% of the weight of the particle.

23. The composition of claim 22, wherein the combined amount of the ammonio methacrylate lacquer and the plasticizer in the rate controlling coating of the first or second quantity of particles is in an amount of 4%, 6%, 8%, 10%, 12%, or 15% of the weight of the particle.

24. The composition of claim 17, wherein the controlled-release of the fluvoxamine is effective in supplying fluvoxamine to the blood of a patient such that, following a single application of the composition to the patient, the amount of circulating fluvoxamine ($AUC_{0-\infty}$) in the blood serum of the patient is about 128 to about 1,175 ng/ml.h.

25. A multiparticulate controlled release selective serotonin reuptake inhibitor (SSRI) composition for oral administration comprising two quantities of particles, each of the particles comprising
 (i) an inert non-pareil core,
 (ii) an SSRI layer comprising fluvoxamine or a pharmaceutically-acceptable salt thereof disposed over the inert core, and
 (iii) a coating of a rate-controlling polymeric acrylate, methacrylate lacquer, or a mixture thereof disposed over the fluvoxamine,
 wherein the composition allows the controlled release of the fluvoxamine over a period of not less than about 12 hours following oral administration, wherein the rate-controlling polymeric acrylate or methacrylate lacquer coating of the first quantity of particles is present in a first amount, and the rate-controlling polymeric acrylate or methacrylate lacquer coating of the second quantity of particles is present in a second amount that is different from the first amount, and wherein the fluvoxamine release rate from the composition exhibits the following in vitro dissolution pattern when measured using a USP type II dissolution apparatus (paddle) according to US Pharmacopeia XXII in 0.05 M phosphate buffer at pH 6.8:
 (a) no more than about 20% of the total fluvoxamine is released after 1 hour of measurement in the apparatus;
 (b) no more than about 45% of the total fluvoxamine is released after 2 hours of measurement in the apparatus;
 (c) between about 20% and about 70% of the total fluvoxamine is released after 4 hours of measurement in the apparatus;
 (d) between about 35% and about 85% of the total fluvoxamine is released after 6 hours of measurement in the apparatus;
 (e) not less than about 50% of the total fluvoxamine is released after 8 hours of measurement in the apparatus;
 (f) not less than about 70% of the total fluvoxamine is released after 10 hours of measurement in the apparatus; and
 (g) not less than about 75% of the total fluvoxamine is released after 12 hours of measurement in the apparatus.

26. The composition of claim 25, wherein the coating is the polymeric acrylate lacquer.

27. The composition of claim 25, wherein the coating is the methacrylate lacquer.

28. The composition of claim 25, wherein the coating is a lacquer which contains a mixture of acrylate and methacrylate.

29. The composition of claim 25, wherein the coating is an acrylic resin comprising a copolymer of acrylic and methacrylic acid esters having a low content of quaternary ammonium groups.

30. The composition of claim 25, wherein the rate-controlling coating comprises an ammonio methacrylate lacquer and a plasticizer, the combined amount of the ammonio methacrylate lacquer and the plasticizer in the membrane coating being in an amount of from about 4% to about 15% of the weight of the particle.

31. The composition of claim 30, wherein the combined amount of the ammonio methacrylate lacquer and the plasticizer in the rate controlling coating of the first or second quantity of particles is in an amount of 4%, 6%, 8%, 10%, 12%, or 15% of the weight of the particle.

32. The composition of claim 25, wherein the controlled-release of the fluvoxamine is effective in supplying fluvoxamine to the blood of a patient such that, following a single application of the composition to the patient, the amount of circulating fluvoxamine ($AUC_{0-\infty}$) in the blood serum of the patient is about 128 to about 1,175 ng/ml.h.

33. A multiparticulate controlled release selective serotonin reuptake inhibitor (SSRI) composition for oral administration comprising two quantities of particles, each of the particles comprising
 (i) an inert non-pareil core,
 (ii) an SSRI layer comprising fluvoxamine or a pharmaceutically-acceptable salt thereof disposed over the inert core, and
 (iii) a coating of a rate-controlling polymeric acrylate, methacrylate lacquer, or a mixture thereof disposed over the fluvoxamine,
 wherein the composition allows the controlled release of the fluvoxamine over a period of not less than about 12 hours following oral administration, wherein the rate-controlling polymeric acrylate or methacrylate lacquer coating of the first quantity of particles is present in a first amount, and the rate-controlling polymeric acrylate or methacrylate lacquer coating of the second quantity of particles is present in a second amount that is different from the first amount, and wherein the fluvoxamine release rate from the composition exhibits the following in vitro dissolution pattern when measured using a USP type II dissolution apparatus (paddle) according to US Pharmacopeia XXII in 0.05 M phosphate buffer at pH 6.8:

(a) no more than about 50% of the total fluvoxamine is released after 2 hours of measurement in the apparatus;
(b) not less than about 35% of the total fluvoxamine is released after 6 hours of measurement in the apparatus; and
(c) not less than about 80% of the total fluvoxamine is released after 22 hours of measurement in the apparatus.

34. The composition of claim 33, wherein the coating is the polymeric acrylate lacquer.

35. The composition of claim 33, wherein the coating is the methacylate lacquer.

36. The composition of claim 33, wherein the coating is a lacquer which contains a mixture of acrylate and methacrylate.

37. The composition of claim 34, wherein the coating is an acrylic resin comprising a copolymer of acrylic and methacrylic acid esters having a low content of quaternary ammonium groups.

38. The composition of claim 33, wherein the rate-controlling coating comprises an ammonio methacrylate lacquer and a plasticizer, the combined amount of the ammonio methacrylate lacquer and the plasticizer in the membrane coating being in an amount of from about 4% to about 15% of the weight of the particle.

39. The composition of claim 38, wherein the combined amount of the ammonio methacrylate lacquer and the plasticizer in the rate controlling coating of the first or second quantity of particles is in an amount of 4%, 6%, 8%, 10%, 12%, or 15% of the weight of the particle.

40. The composition of claim 33, wherein the controlled-release of the fluvoxamine is effective in supplying fluvoxamine to the blood of a patient such that, following a single application of the composition to the patient, the amount of circulating fluvoxamine ($AUC_{0-\infty}$) in the blood serum of the patient is about 128 to about 1,175 ng/ml.h.

41. A method for the treatment of depression or obsessive compulsive disorder treatable with an SSRI, comprising administering to a patient suffering from one of the conditions a therapeutically effective amount of a multiparticulate controlled release selective serotonin reuptake inhibitor (SSRI) composition for oral administration comprising two quantities of particles, each of the particles comprise
  (i) an inert non-pareil core,
  (ii) an SSRI layer comprising fluvoxamine or a pharmaceutically-acceptable salt thereof disposed over the inert core, and
  (iii) a coating of a rate-controlling polymeric acrylate, methacrylate lacquer, or a mixture thereof disposed over the fluvoxamine,
  wherein the composition allows the controlled release of the fluvoxamine over a period of not less than about 12 hours following oral administration, and wherein the rate-controlling polymeric acrylate or methacrylate lacquer coating of the first quantity of particles is present in a first amount, and the rate-controlling polymeric acrylate or methacrylate lacquer coating of the second quantity of particles is present in a second amount that is different from the first amount, and wherein the fluvoxamine release rate from the composition exhibits the following in vitro dissolution pattern when measured using a USP type II dissolution apparatus (paddle) according to US Pharmacopeia XXII in 0.05 M phosphate buffer at pH 6.8:
  (a) no more than about 15% of the total fluvoxamine is released after 0.5 of an hour of measurement in the apparatus;
  (b) no more than about 25% of the total fluvoxamine is released after 1 hour of measurement in the apparatus;
  (c) between about 20% and 75% of the total fluvoxamine is released after 2 hours of measurement in the apparatus;
  (d) not less than about 75% of the total fluvoxamine is released after 4 hours of measurement in the apparatus; and
  (e) not less than about 85% of the total fluvoxamine is released after 6 hours of measurement in the apparatus.

42. A method for the treatment of depression or obsessive compulsive disorder treatable with an SSRI, comprising administering to a patient suffering from one of the conditions a therapeutically effective amount of a multiparticulate controlled release selective serotonin reuptake inhibitor (SSRI) composition for oral administration comprising two quantities of particles, each of the particles comprise
  (i) an inert non-pareil core,
  (ii) an SSRI layer comprising fluvoxamine or a pharmaceutically-acceptable salt thereof disposed over the inert core, and
  (iii) a coating of a rate-controlling polymeric acrylate, methacrylate lacquer, or a mixture thereof disposed over the fluvoxamine,
  wherein the composition allows the controlled release of the fluvoxamine over a period of not less than about 12 hours following oral administration, and wherein the rate-controlling polymeric acrylate or methacrylate lacquer coating of the first quantity of particles is present in a first amount, and the rate-controlling polymeric acrylate or methacrylate lacquer coating of the second quantity of particles is present in a second amount that is different from the first amount, and wherein the fluvoxamine release rate from the composition exhibits the following in vitro dissolution pattern when measured using a USP type II dissolution apparatus (paddle) according to US Pharmacopeia XXII in 0.05 M phosphate buffer at pH 6.8:
  (a) no more than about 20% of the total fluvoxamine is released after 4 hours of measurement in the apparatus;
  (b) no more than about 45% of the total fluvoxamine is released after 6 hours of measurement in the apparatus;
  (c) between about 45% and 80% of the total fluvoxamine is released after 8 hours of measurement in the apparatus;
  (d) not less than about 70% of the total fluvoxamine is released after 10 hours of measurement in the apparatus; and
  (e) not less than about 80% of the total fluvoxamine is released after 12 hours of measurement in the apparatus.

43. A method for the treatment of depression or obsessive compulsive disorder treatable with an SSRI, comprising administering to a patient suffering from one of the conditions a therapeutically effective amount of a multiparticulate controlled release selective serotonin reuptake inhibitor (SSRI) composition for oral administration comprising two quantities of particles, each of the particles comprise
  (i) an inert non-pareil core,
  (ii) an SSRI layer comprising fluvoxamine or a pharmaceutically-acceptable salt thereof disposed over the inert core, and
  (iii) a coating of a rate-controlling polymeric acrylate, methacrylate lacquer, or a mixture thereof disposed over the fluvoxamine,
  wherein the composition allows the controlled release of the fluvoxamine over a period of not less than about 12 hours following oral administration, and wherein the rate-controlling polymeric acrylate or methacrylate lacquer coating of the first quantity of particles is present in a first amount, and the rate-controlling polymeric acrylate or methacrylate lacquer coating of the second quantity of particles is present in a second amount that is different from the first amount, and wherein the fluvoxamine release rate from the composition exhibits the following in vitro dissolution pattern when measured using a USP type II dissolution apparatus (paddle) according to US Pharmacopeia XXII in 0.05 M phosphate buffer at pH 6.8:
(a) no more than 20% of the total fluvoxamine is released after 1 hour of measurement in the apparatus;
(b) no more than 60% of the total fluvoxamine is released after 2 hours of measurement in the apparatus;
(c) not less than 20% of the total fluvoxamine is released after 4 hours of measurement in the apparatus;
(d) not less than 35% of the total fluvoxamine is released after 6 hours of measurement in the apparatus;
(e) not less than 50% of the total fluvoxamine is released after 8 hours of measurement in the apparatus;
(f) not less than 70% of the total fluvoxamine is released after 10 hours of measurement in the apparatus; and
(g) not less than 75% of the total fluvoxamine is released after 12 hours of measurement in the apparatus.

44. A method for the treatment of depression or obsessive compulsive disorder treatable with an SSRI, comprising administering to a patient suffering from one of the conditions a therapeutically effective amount of a multiparticulate controlled release selective serotonin reuptake inhibitor (SSRI) composition for oral administration comprising two quantities of particles, each of the particles comprise
   (i) an inert non-pareil core,
   (ii) an SSRI layer comprising fluvoxamine or a pharmaceutically-acceptable salt thereof disposed over the inert core, and
   (iii) a coating of a rate-controlling polymeric acrylate, methacrylate lacquer, or a mixture thereof disposed over the fluvoxamine,
   wherein the composition allows the controlled release of the fluvoxamine over a period of not less than about 12 hours following oral administration, and wherein the rate-controlling polymeric acrylate or methacrylate lacquer coating of the first quantity of particles is present in a first amount, and the rate-controlling polymeric acrylate or methacrylate lacquer coating of the second quantity of particles is present in a second amount that is different from the first amount, and wherein the fluvoxamine release rate from the composition exhibits the following in vitro dissolution pattern when measured using a USP type II dissolution apparatus (paddle) according to US Pharmacopeia XXII in 0.05 M phosphate buffer at pH 6.8:
   (a) no more than about 20% of the total fluvoxamine is released after 1 hour of measurement in the apparatus;
   (b) no more than about 45% of the total fluvoxamine is released after 2 hours of measurement in the apparatus;
   (c) between about 20% and about 70% of the total fluvoxamine is released after 4 hours of measurement in the apparatus;
   (d) between about 35% and about 85% of the total fluvoxamine is released after 6 hours of measurement in the apparatus;
   (e) not less than about 50% of the total fluvoxamine is released after 8 hours of measurement in the apparatus;
   (f) not less than about 70% of the total fluvoxamine is released after 10 hours of measurement in the apparatus; and
   (g) not less than about 75% of the total fluvoxamine is released after 12 hours of measurement in the apparatus.

45. A method for the treatment of depression or obsessive compulsive disorder treatable with an SSRI, comprising administering to a patient suffering from one of the conditions a therapeutically effective amount of a multiparticulate controlled release selective serotonin reuptake inhibitor (SSRI) composition for oral administration comprising two quantities of particles, each of the particles comprise
   (i) an inert non-pareil core,
   (ii) an SSRI layer comprising fluvoxamine or a pharmaceutically-acceptable salt thereof disposed over the inert core, and
   (iii) a coating of a rate-controlling polymeric acrylate, methacrylate lacquer, or a mixture thereof disposed over the fluvoxamine,
   wherein the composition allows the controlled release of the fluvoxamine over a period of not less than about 12 hours following oral administration, and wherein the rate-controlling polymeric acrylate or methacrylate lacquer coating of the first quantity of particles is present in a first amount, and the rate-controlling polymeric acrylate or methacrylate lacquer coating of the second quantity of particles is present in a second amount that is different from the first amount, and wherein the fluvoxamine release rate from the composition exhibits the following in vitro dissolution pattern when measured using a USP type II dissolution apparatus (paddle) according to US Pharmacopeia XXII in 0.05 M phosphate buffer at pH 6.8:
   (a) no more than about 50% of the total fluvoxamine is released after 2 hours of measurement in the apparatus;
   (b) not less than about 35% of the total fluvoxamine is released after 6 hours of measurement in the apparatus; and
   (c) not less than about 80% of the total fluvoxamine is released after 22 hours of measurement in the apparatus.

* * * * *